United States Patent [19]

Plomgren et al.

[11] Patent Number: 5,224,137
[45] Date of Patent: Jun. 29, 1993

[54] TUNING THE SCANNING ELECTRON BEAM COMPUTED TOMOGRAPHY SCANNER

[75] Inventors: Susan E. Plomgren, Twinview; John L. Couch; Mark C. Nicely, both of San Francisco; Roy E. Rand, Palo Alto, all of Calif.

[73] Assignee: Imatron, Inc., So. San Francisco, Calif.

[21] Appl. No.: 705,575

[22] Filed: May 23, 1991

[51] Int. Cl.[5] .............................................. H05G 1/52
[52] U.S. Cl. ..................... 378/10; 378/137; 378/138; 378/113
[58] Field of Search .............. 328/10, 9, 12, 119, 328/124, 137, 138, 113, 16, 205; 256/396 R, 397, 398, 399, 491.1

[56] References Cited

U.S. PATENT DOCUMENTS

| | | | |
|---|---|---|---|
| 3,895,234 | 7/1975 | O'Keeffe et al. | 250/397 |
| 4,521,901 | 6/1985 | Rand | 378/123 |
| 4,631,741 | 12/1986 | Rand et al. | 378/10 |

Primary Examiner—David P. Porta
Attorney, Agent, or Firm—Flehr, Hohbach, Test, Albritton & Herbert

[57] ABSTRACT

A scanning electron beam computed tomography scanner is disclosed herein and includes means defining a vacuum chamber, means for producing an electron beam at one location in the chamber and for directing it to a second location therein, a target located at a third position therein of the type which produces X-rays as a result of the impingement thereon by the electron beam, means for focusing the beam onto the target in the form of a beam spot and for scanning the beam spot across the target along a particular scan path in order to produce X-rays, and means for monitoring the profile, position, and orientation of the beam spot at a plurality of locations along the scan path. The specific scanner disclosed also includes an arrangement for determining from the signals produced by the monitoring devices if the beam spot conforms to as desired profile, position, and orientation and automatically adjusting the electron beam such that its profile, position, and orientation conform to desired values.

56 Claims, 12 Drawing Sheets

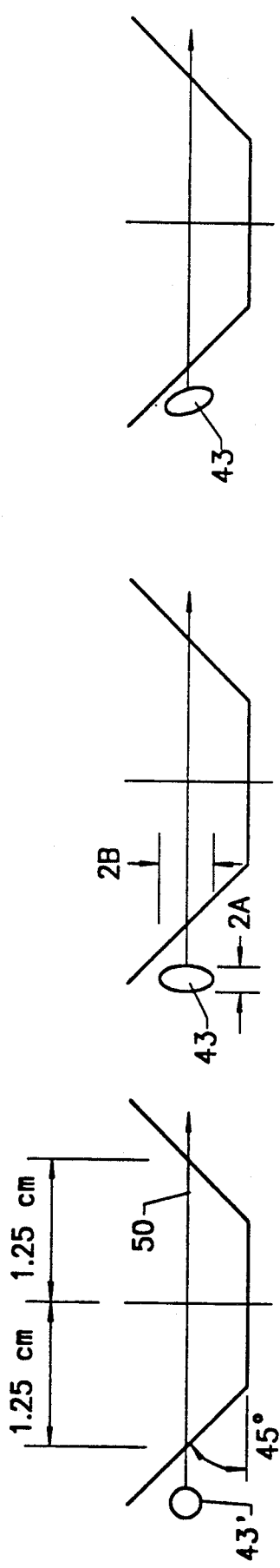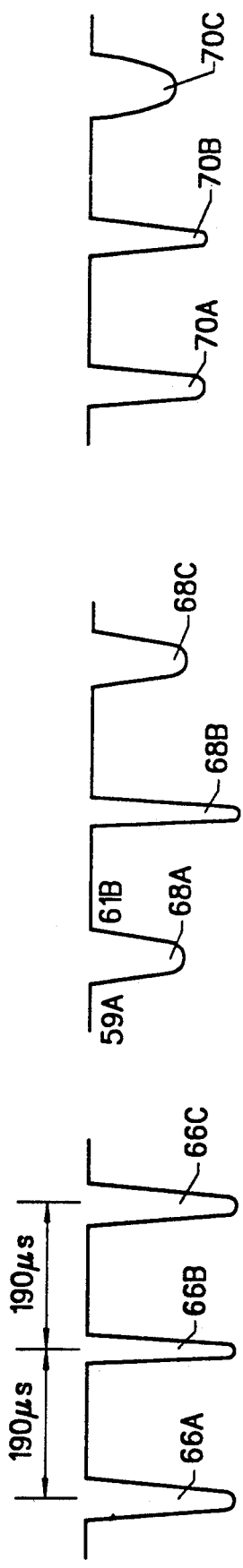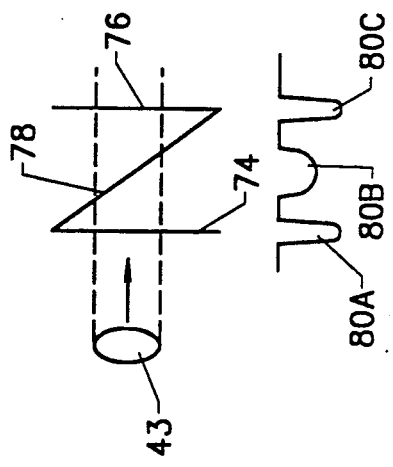
FIG. 5A   FIG. 5B   FIG. 5C
FIG. 6

LOAD NEW DCC'S TO ADJUST BEAM — 119

SCAN SERVER (HARDWARE CHECKS,
POWER SUPPLY TIMEOUT;
RETRIES)

CREATE NEW DEFLECTION BUFFER FROM NEW DCC'S
TAKE SET (OR SETS FOR AVERAGING) OF SCANS;
STORE DAS W-WIRE DATA INTO MEMORY;
DISPLAY W-WIRE PROFILES IF REQUESTED.

(CONTINUE) — OPTIMIZATION OF CHARACTERISTIC (I) LOOP

120 — IS CURRENT OVERALL QUALITY > PREVIOUS QUALITY?
- Y → 121 STORE NEW STATE OF BEAM
- N (CONTINUE)

BEAM CHARACTERISTICS LOOP

122 — IS QUALITY OF OVERALL BEAM WITHIN SPECIFICATIONS?
- Y → 124 EXIT → 125 OUTPUT SUMMARY OF BEAM QUALITY
- N → 123 DID OVERALL STATE OF BEAM IMPROVE?
  - Y → 126 STORE OVERALL STATE OF BEAM → (CONTINUE SCAN) — 128 → (C)
  - N → EXIT

127 GLOBAL OPTIMIZATION

OUTER INTERATIVE LOOP

TUNING THE SCANNING ELECTRON BEAM COMPUTED TOMOGRAPHY SCANNER

BRIEF DESCRIPTION OF THE INVENTION

The present invention relates generally to a scanning electron beam computed tomography scanner including means of controlling the shape and position of an electron beam as it scans across a target for the purpose of producing X-rays. The present invention also relates generally to a method of controlling the shape and position of an electron beam as it scans across a target for the purpose of producing X-rays in a scanning electron beam computed tomography scanner.

BACKGROUND OF THE INVENTION

The present invention is suitable for use with the scanning electron beam computed tomography scanner disclosed in U.S. Pat. No. 4,521,901 which has been assigned to the assignee of the present application. This patent discloses a scanner including a vacuum chamber, an electron gun for producing an electron beam at one end of the chamber, and means for causing the electron beam to scan along an elongated target spaced from the electron gun located within the other end of the chamber. The electron beam impinges on the target and produces X-rays. This patent also discloses a means for causing the cross section of the electron beam—hereafter referred to as the beam spot—at its point of impingement on the target to be generally elliptical in configuration.

U.S. Pat. No. 4,631,741 discloses a method for monitoring the profile, position and orientation of the beam spot at a plurality of positions along the target to determine if the actual profile, position and orientation of the beam spot are equal to the desired profile, position and orientation of the beam spot at these various positions along the target. This method comprises locating a series of electron beam intercepting devices at various points in front of the target, each of which is designed to produce an electrical signal upon impingement of the beam such that the configuration of this signal varies with the profile, position and orientation of the beam as the beam impinges the device. These signals are processed and directed to an oscilloscope which is viewed by an operator who makes corrections to the electron beam direction and shape in order to maintain the desired beam spot profile, position, and orientation. This method is governed by a "trial and error" approach and requires a highly trained technical expert. As a result, the tuning process is extremely slow. The present application more clearly defines the process of correcting the electron beam in order to maintain the desired beam spot behavior and is performed quickly and can be performed automatically without any input from the user.

SUMMARY AND OBJECTS OF THE INVENTION

It is the general object of this invention to control the characteristics of the electron beam as it scans across an X-ray producing target in a scanning electron beam computed tomography scanner.

A more particular object of this invention is to control the characteristics of the electron beam in a scanning electron beam computed tomography scanner such that the profile, position, and orientation of the electron beam spot conform to the desired profile, position, and orientation of the beam spot at various positions along the X-ray producing target.

It is another specific object of this invention to quantitatively characterize the beam profile by extracting information from electron beam intercepting devices which are placed at a plurality of monitoring points in front of the X-ray producing target.

A more particular object of this invention is to control the characteristics of the electron beam by adjusting the electric current traveling through magnets in a deflection system which focuses the electron beam onto and causes it to scan along the length of the X-ray producing target.

It is another specific object of this invention to adjust the profile, position, and orientation of the electron beam using known relationships between the information extracted from the electron beam intercepting devices and the electrical currents through the deflection magnets.

It is another specific object of this invention to compute a continuous curve that directs the flow of currents through the deflection magnets in order to direct the electron beam across the X-ray producing target while maintaining the desired shape, position, and orientation of the electron beam spot.

It is another specific object of the invention to quantitatively define the overall quality of the electron beam which is a function of the current state of the beam and the desired state of the beam.

The attainment of these and related objects are achieved by placing electron beam intercepting devices at a plurality of monitoring points along a scan path immediately in front of an X-ray producing target in a scanning electron beam computerized tomography scanner. Each of these devices produce an electrical signal which varies with the shape, position, and orientation of the electron beam spot created as the beam impinges on the target. The resulting signals from each of the intercepting devices are sent to a computing means which quantitatively characterizes the profile, position, and orientation of the beam spot along the scan path. Using this computed characterization of the electron beam, the computing means then calculates the necessary adjustments to the electrical currents through a deflection system to cause the electron beam to conform to the desired profile, position, and orientation. The overall quality of the electron beam is computed as the electrical currents are being adjusted. This process of updating the state of the electron beam by adjusting the electrical currents through the deflection system continues until the overall computed quality of the electron beam is within predetermined specifications, or until a specified number of iterations have been performed.

BRIEF DESCRIPTION OF THE DRAWINGS

The foregoing and other related objects and features of advantage of the invention should be more readily apparent to those skilled in the art, after review of the following more detailed description of the invention, taken together with the accompanying drawings which:

FIG. 5a, 5b, 5c, and 6 illustrate the beam intercepting devices of FIG. 3 and the resulting electrical signals which are created by the impingement of the electron beam thereupon.

FIGS. 12a, 12b, and 12c are a block diagram showing generally the method of tuning the electron beam.

DETAILED DESCRIPTION OF THE PREFERRED EMBODIMENTS

Figure 1:
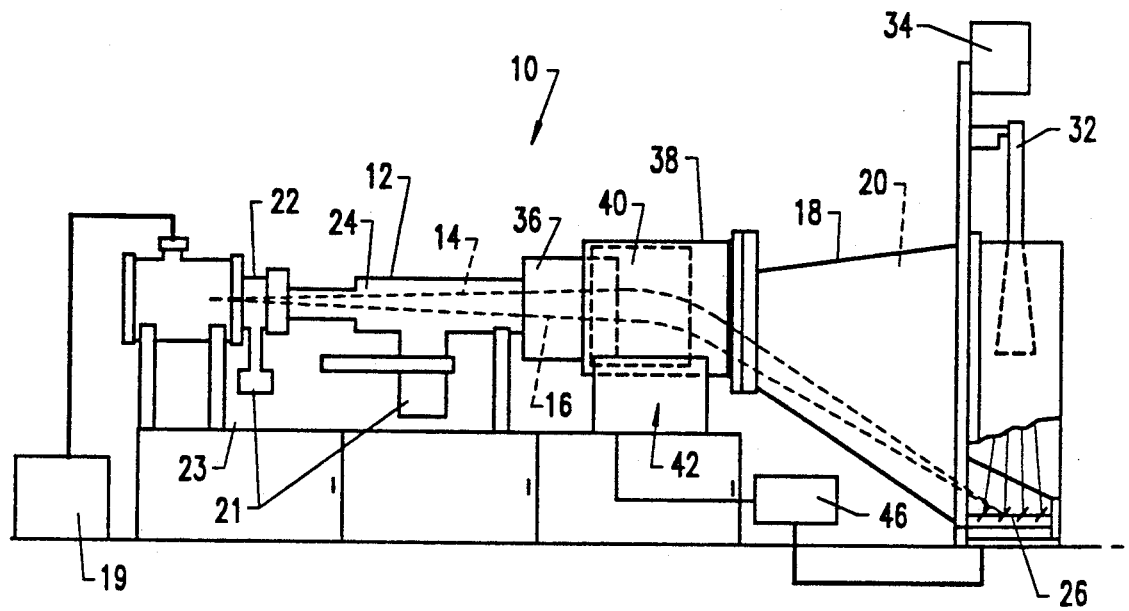
FIG. 1 illustrates a scanning electron beam computed tomography scanner including a beam spot controlling arrangement designed in accordance with the present invention.

FIG. 1 illustrates a scanning electron beam computed tomography scanner, generally indicated by the numeral 10. This scanner may be identical to the scanner disclosed in U.S. Pat. No. 4,631,741 except for the electron beam controlling means which forms the present invention. Therefore, the specific features which form the scanner, except those that are directly related to the present invention, will not be disclosed in detail here.

The scanner generally indicated in FIG. 1 by reference numeral 10 includes means defining one section of a vacuum chamber 16 generally indicated by 14, means for producing an electron beam 24 using an electron gun 22 located at the rearwardmost end of chamber 16, means for providing a high voltage electrical power supply to the electron gun 19, means for directing the beam horizontally to the forwardmost end of the chamber 14, and means generally indicated at 20 for defining a second section of chamber 16 which tapers downward and outward from chamber section 14.

Figure 2:
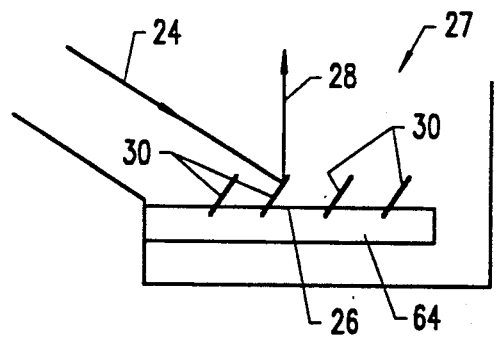
FIG. 2 shows a side view of an X-ray producing target assembly which is an inherent part of the scanner shown in FIG. 1.

In addition, the scanner 10 includes an assembly of targets generally indicated at 26 in FIG. 1 and more specifically in FIG. 2 located at the forwardmost end of chamber section 20 of the type which produce X-rays 28 as a result of the impingement thereon by the electron beam 24. The targets indicated at 30 in FIG. 2 are generally curved as shown on FIG. 3 and extend around the inside of chamber section 20 and face the rearwardmost end of chamber 20 in order to be impinged upon by electron beam 24, thus producing X-rays 28 which are directed upward toward the detectors 32.

Scanner 10 in FIG. 1 also includes a focusing and scanning arrangement or deflection system generally indicated by 42 at the forwardmost end of chamber section 16 and the rearwardmost end of chamber section 20 further comprising a solenoid coil 36 and an assembly of dipole coils 38, the latter containing a set of magnetic quadrupole coils 40 for focusing the electron beam 24 onto and causing it to scan along the length of one of the targets 30 to cause X-rays 28 to be produced and emanate from the target. Although the deflection system referred to in this application is of the type described above, the deflection system could be any device which affects the characteristics of the electron beam spot. A possible alternative to the deflection system described above would be an electrical field focusing device.

As described in U.S. Pat. No. 4,521,901, and shown in FIG. 3, the cross section 43 of the electron beam 24 as it impinges upon the target 30 is generally elliptical in shape, the major axis of which is normal to the scan path and extends in the radial direction indicated by R, while its minor axis extends in the azimuth direction A. This desired elliptical beam spot is created by the quadrupole coils 40 in combination with the dipole coils 38 which focus the electron beam to a spot on the target utilizing differential focal strength optics. This focusing mechanism maintains the desired elliptical shaped beam spot at all points along the scan path.

Scanner 10 also includes in accordance with the invention means generally indicated by 26 in FIG. 1 for monitoring the actual shape and position of the electron beam spot on the target. The apparatus 26 includes a series of electron beam intercepting devices more specifically indicated by 52 in FIG. 3 located at various points in front of the target 30 which produce an electrical signal upon impingement by the beam as the beam scans across the target 30 such that the configuration of this signal varies with the position and shape of the electron beam spot.

Figure 7:
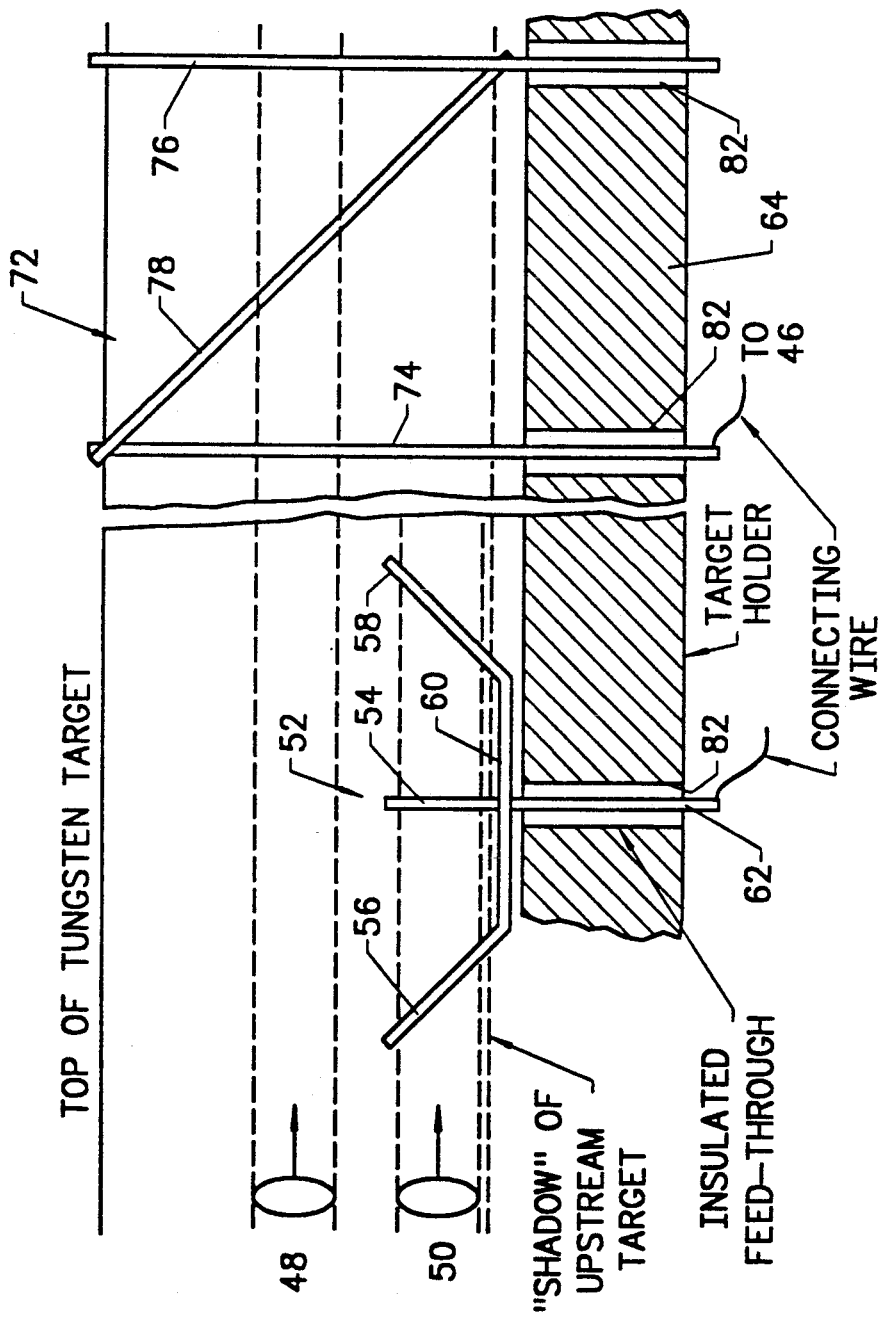
FIG. 7 shows a detailed view of two types of beam intercepting devices and the way in which they are attached to the target support of FIG. 2.

This electron beam intercepting device, more specifically illustrated in FIG. 7 and generally indicated by 52, is in the form of a generally W-shaped electrically conductive wire, preferably made of tungsten, having three segments which are spaced apart including a central segment 54 and two opposite end segments 56 and 58 which extend away from the central segment. The two opposite end segments are joined by a common base segment 60 which is welded to the central segment. Attached to the central segment is a connecting wire 62 which extends through a cooperating insulated passage through base 64 on which the device 52 is supported to computer processing means 46 (FIG. 1). The straight segment 54 orthogonally extends across monitoring path 50 and the end segments 56 and 58 extend across the path at angles of 45°. The base segment 60 lies outside of the scan path 50.

Figure 3:
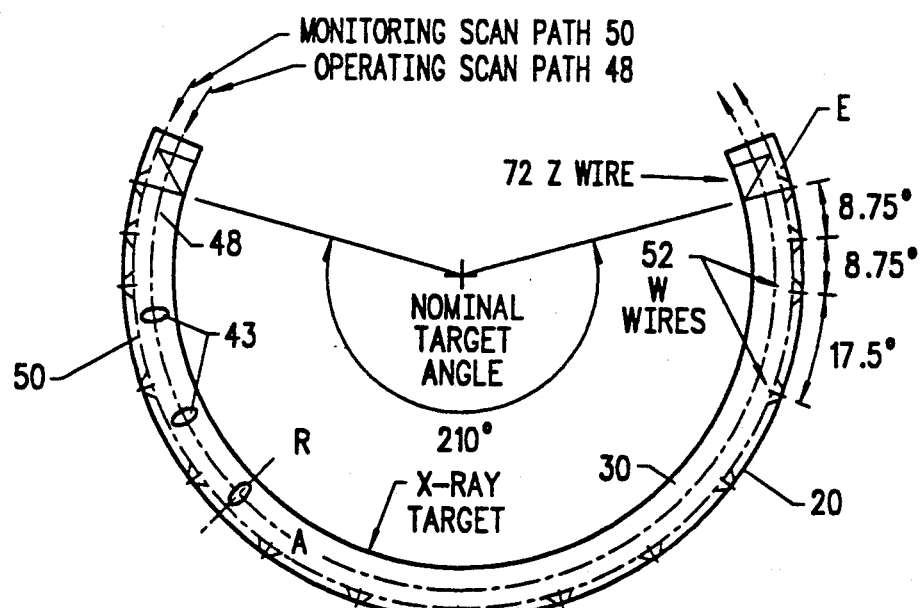
FIG. 3 shows a cross-sectional view of one of the targets forming part of the overall target assembly of FIG. 2 including specifically a plurality of electron beam intercepting devices forming part of the overall beam spot controlling arrangement disclosed herein.
Figure 4:
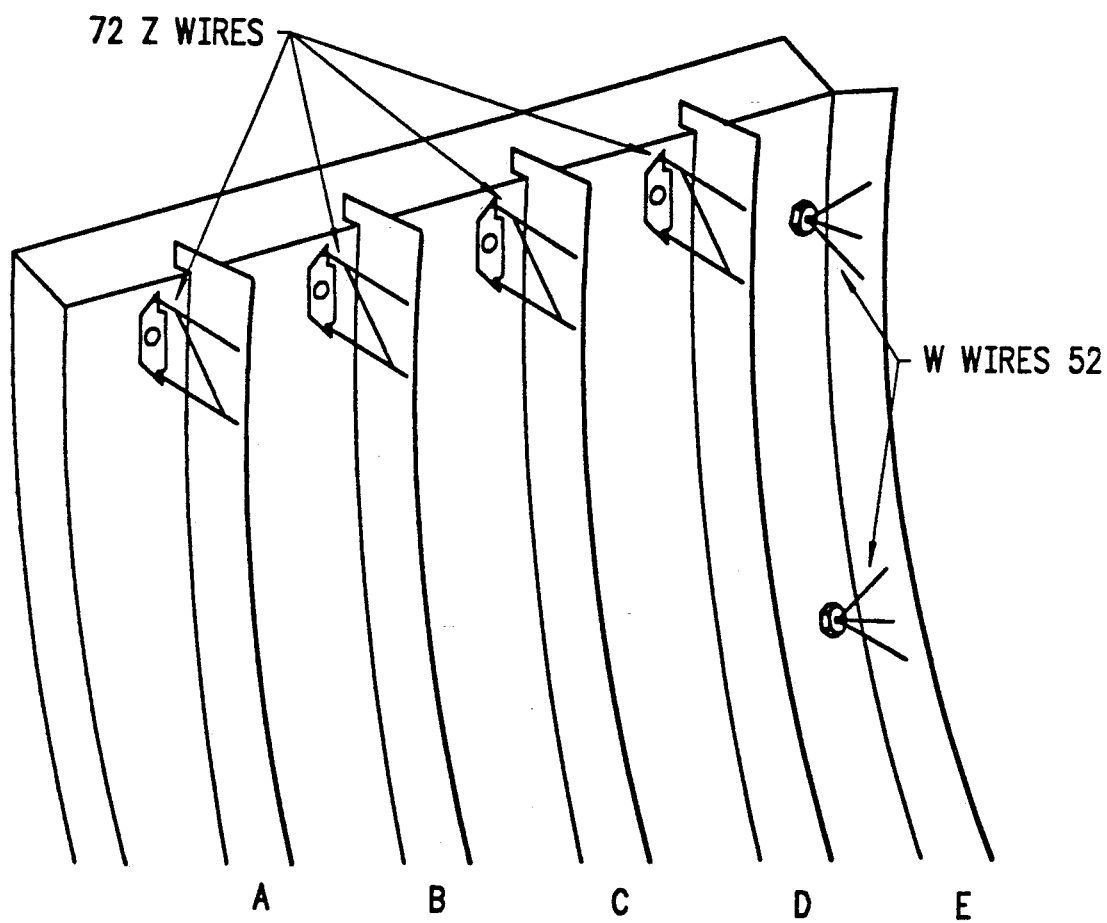
FIG. 4 shows a plurality of X-ray producing targets and the positional relationship between the electron beam intercepting devices and the targets.
Figure 8:
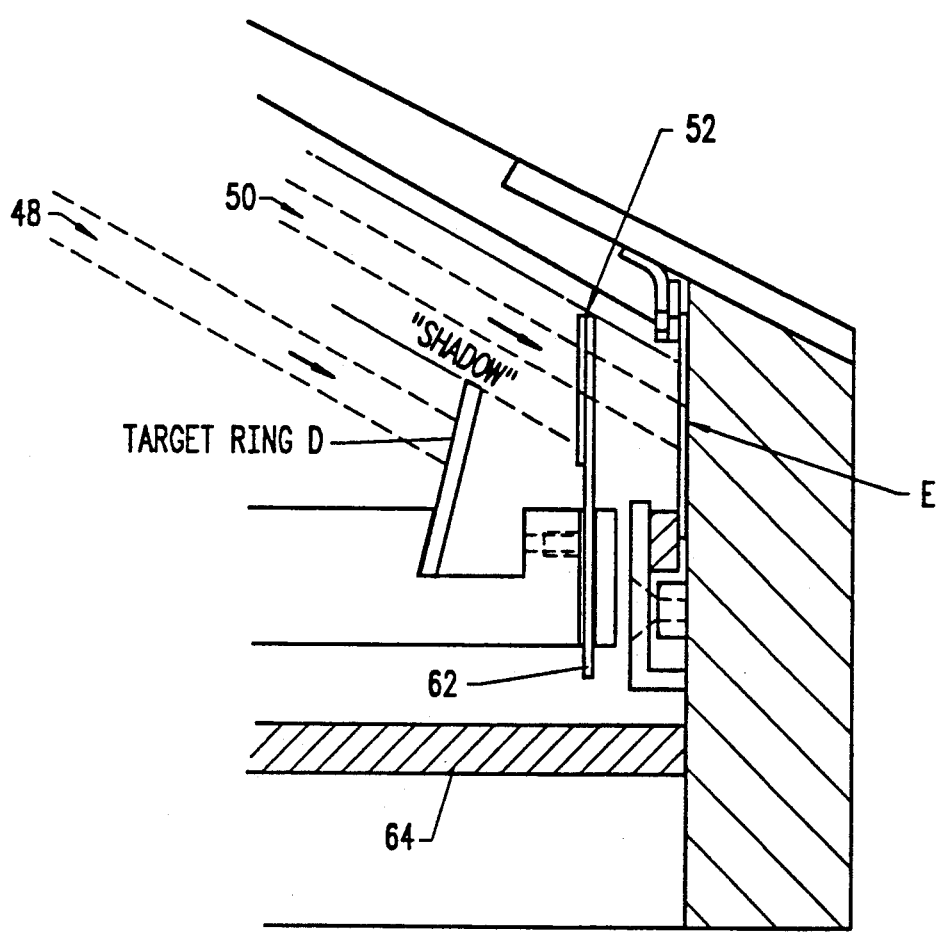
FIG. 8 is a more detailed side view of the target assembly shown in FIG. 2 specifically illustrating the positional relationship between the X-ray producing targets and a particular electron beam intercepting device.

Each target ring 30 extends the length of the target as indicated in FIG. 3. The radially outer target, labeled as target ring E in FIGS. 3 and 4, serves as a monitoring path along which the electron beam impinges the intercepting devices 52 located in front of the target ring E at a plurality of locations along the scan path thereby producing electrical signals which are used to establish the desired position and shape of the electron beam spot as indicated in FIGS. 3 and 7. The radially inner targets, labeled target rings A, B, C, and D in FIG. 4, which do not include any w-wire electron beam intercepting devices, are used as the operating scan paths 48 in that X-rays are produced and directed towards the detectors 32 as the electron beam scans along this path. Scan path 48 in FIGS. 3, 7, and 8 is representative of one of the possible operational scan paths. While not shown, means are included for acting on the electron beam such that the beam spot 43 shifts radially between the two scan paths 50 and 48. Different types of beam intercepting devices are located at each end of the operating scan path 48 which are used to monitor the new radius of the new scan path in order to determine if this shift has been correctly made, as shown in FIGS. 3 and 4.

As stated above, the electrical signals produced by the intercepting devices 52 upon impingement by the beam as the beam scans across the target 30 vary with the position and shape of the beam spot at that particular device. Consider first a circular beam spot indicated as 43' in FIG. 5a which is perfectly aligned radially. The resulting electrical signal produced as the electron beam scans past device 52 consists of three pulses 66a, 66b, and 66c of equal height. However, because the outer wire segments 56 and 58 extend across path 50 at 45° angles, the outside pulses 66a and 66c are $\sqrt{2}$ times the width of central pulse 66b. Because the three segments 54, 56 and 58 are fixed in position relative to one another and because the outer segments extend at an angle relative to the central segment, the spatial relationship between the pulses 66 will vary with the radial (lateral) position of beam spot 43 on path 50 (that is, the vertical position of the beam spot as it is viewed in FIG. 5), assuming that the scan speed of the beam spot is fixed. Thus, with the outer segments 56 and 58 disposed at 45° relative to the central segment 54 and with the three segments spaced relative to one another in the manner illustrated, that is, such that a central point on each outer segment is 1.25 cm from the central segment and further assuming a constant scan velocity of 65 m/s, for a perfectly aligned beam, that is, one which moves across the center of the scan path as illustrated in FIG. 5a, the three pulses will be separated by 190 microseconds. If the beam spot crosses device 52 at points further away from base segment 60, the time between pulses will increase and if the beam spot is closer to base segment 60, the time between pulses will decrease. This information can be utilized to adjust the electron beam in order to place the beam spot in the center of its scan path. Unequal spacings between the pulses 66 would indicate that the actual scan path taken by the beam spot has a radial component and can be corrected likewise. Moreover, the time of arrival of the beam spot at the device 52, that is the azimuthal (longitudinal) position of the beam spot, can be measured by comparing the pulses 66 for each device 52 with a timing pulse generated by a computer which controls the operation of the overall scanner. Computer processing means 46 can comprise such means for generating timing pulses. If the timing pulses and pulses 66 are in sync with one another in a predetermined way, the beam spot is at the right place at the right time. In other words, it is in the desired longitudinal position. Thus, by observing these two types of pulses, the longitudinal position of the beam spot can be monitored.

The foregoing has been a discussion of the way in which a circular beam spot interacts with an electron beam intercepting device 52. While the present invention is compatible with a scanning electron beam having a circular beam spot, the (preferred) scanner also provides a preferred elliptical beam spot, as discussed previously. Moreover, this preferred beam spot has its major axis in the scanner's radial direction, that is, perpendicular to the scan path while its minor axis is in the azimuthal direction. The interaction between this beam spot and the same device 52 shown in FIG. 5a is illustrated in FIG. 5b along with corresponding output pulses (oscilloscope traces) 68a, 68b, and 68c. For this example, it is assumed that the beam spot is properly oriented so that its major axis is normal to the scan path and the beam spot is centrally located on the scan path. Further, the minor axis is assumed to be equal to $2a$ while the major axis is assume to be equal to $2b$, as illustrated. Therefore, the ratio of the height of each outside pulse 68a to inner pulse 68b is $\sqrt{2}a/\sqrt{a^2+b^2}:1$, while the width of the inner pulse is a measure of $2a$ and the width of the outer pulses is a measure of $2\sqrt{a^2+b^2}$ in the same units. As in the case of the circular beam spot, if the elliptical beam spot varies laterally (radially) within the scan path, the pulses 68 will either move closer together or further apart.

FIG. 5c shows how the beam intercepting device 52 interacts with beam spot 43 when the latter is incorrectly oriented, that is, skewed counterclockwise as shown. In this case, the first two pulses which are indicated at 70a and 70b mimic the pulses 66a and 66b corresponding to the circular beam spot 43' while the third pulse 70c is shorter and wider. If the beam spot is skewed in the opposite direction, the pulse 70a would be the shorter and wider one.

Returning to FIG. 3, it should be apparent in view of the foregoing that the various devices 52 positioned along scan path 50 in front of target 26 can be used to monitor the profile and position (laterally) of the beam spot on the path and its orientation (assuming a noncircular beam spot) by producing corresponding pulses of the type described by FIGS. 5a-5c. At the same time, these pulses can be used to correct for errors in the profile of the beam spot, its orientation and its position both laterally and longitudinally (e.g., the beam spot's time of arrival at the various devices 52) on the monitoring scan path.

After the beam spot is focused, aligned and properly positioned on monitoring path 50 at each device 52, it path radius is decreased by a known amount at each device in order to define the previously recited operating scan path 48. This latter path is monitored by two generally Z-shaped electron beam intercepting devices 72 which are located at opposite ends of scan path 48 directly in front of the target surface 30. The right hand most one of these devices (as viewed in FIG. 3) is illustrated in FIG. 7. Device 72 is made up of three segments of an electrically conductive wire, preferably a tungsten wire, opposite end segments 74 and 76 and a central segment 78. This device is supported to base 64 in the same manner as the devices 52 with the segments 74 and 76 extending there through in an electrically insulated fashion. One or both of these segments extend to processing means 46 through connecting wire 62.

As illustrated both in FIGS. 3 and 7, both of the outer segments 74 and 76 of each of the devices 72 extend across operating scan path 48 in directions normal thereto. At the same time, the central segment extends across the scan path at an angle thereto, specifically at an angle of 45° in the particular embodiment shown. FIG. 6 shows how the beam spot 43 interacts with each of the devices 72. For purposes of illustration, the elliptical spot 43 is shown in FIG. 6 at the proper orientation and the desired location on the scan path (the central location laterally). Under these conditions, three pulses 80a, 80b, and 80c are produced equidistant from one another. If the beam spot is laterally further from base 64 than the desired scan path, then the pulses 80a and 80b will be closer together than the pulses 80b and 80c. On the other hand, if the beam spot is closer to base 64, the beam spots 80b and 80c will be closer than the beam spots 80a and 80b. If the beam spot is incorrectly oriented, the pulses would change in a manner corresponding to the pulses 70 in FIG. 5c.

The foregoing has been a description of an overall beam spot monitoring arrangement generally for use in a scanning electron beam computed tomography scanner. In an actual working embodiment, the electrically conductive wire segments making up devices 52 and 72 are constructed of tungsten wire 0.030 inch in diameter, spot welded together. The segments extending through base 64 are preferably insulated by means of glass or ceramic grommets 82. In the case of the w-shaped devices 52, in order to prevent the base segment of each from being subjected to the electron beam, the base is located outside the beam path. In the case of a multi-target assembly such as assembly 27 (FIG. 2), the devices 52 are positioned such that their respective base segments 60 lie within the "shadow" of the upstream target, as illustrated in FIG. 8. From the information derived from these devices, the necessary shifts can be computed and made to the electron beam to operate properly across the other targets. FIG. 8 also shows how a device 52 is located well away from the operating scan path 48 and outside the range of X-ray collimators so that should any stray electrons hit the devices 52, the x-rays produced cannot reach the scanner detectors 32.

Electrically, the wire segments making up the devices 52 and 72 are connected in groups and grounded through 50 ohm resistors. Thus, for a beam current of 600 milliamps and assuming a secondary emission coefficient of 0.5 and a beam spot width of 0.080 inch (2 millimeters), the maximum amplitude of the electrical signal is expected to be about 5 volts. In practice this amplitude is reduced by the conductivity of the plasma which is created by the electron beam.

It should be noted that the scanner generally indicated by the reference numeral 10 in FIG. 1 may include other components which do not form part of the present invention but which are necessary or desirable to the operation of the overall scanner.

The foregoing has been a general description of the overall scanning electron beam computed tomography scanner including a beam spot monitoring arrangement. The present invention is specifically directed to the method of controlling the characteristics of the electron beam spot 43 as it scans across a target for the purpose of producing X-rays. The electrical signals produced by the electron beam intercepting devices 52 upon impingement of the electron beam 24 as the beam scans along the target 30 are used to characterize the present state of the electron beam. This characterization is compared to a predetermined desired state of the electron beam. The difference between the present characteristics and the desired characteristics are used to compute adjustments to the electrical currents in the coils 36, 38, and 40 in the focusing and scanning arrangement 42 which will correct the state of the electron beam. This method is generally illustrated in FIG. 12.

Figure 12A:
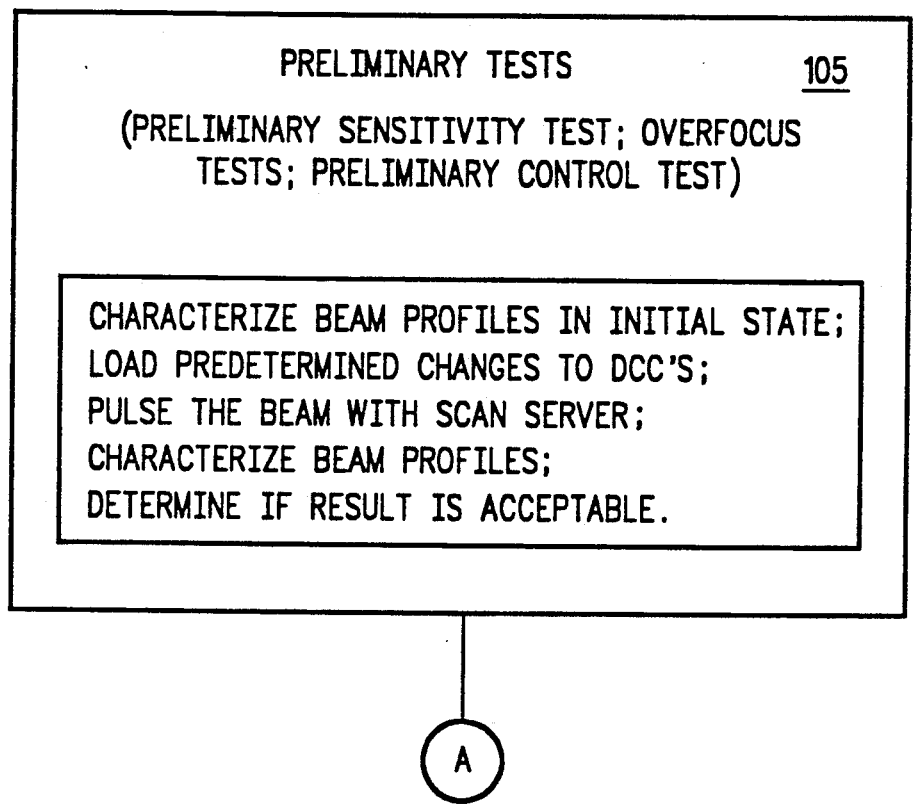
Figures 1, 2, 12B:
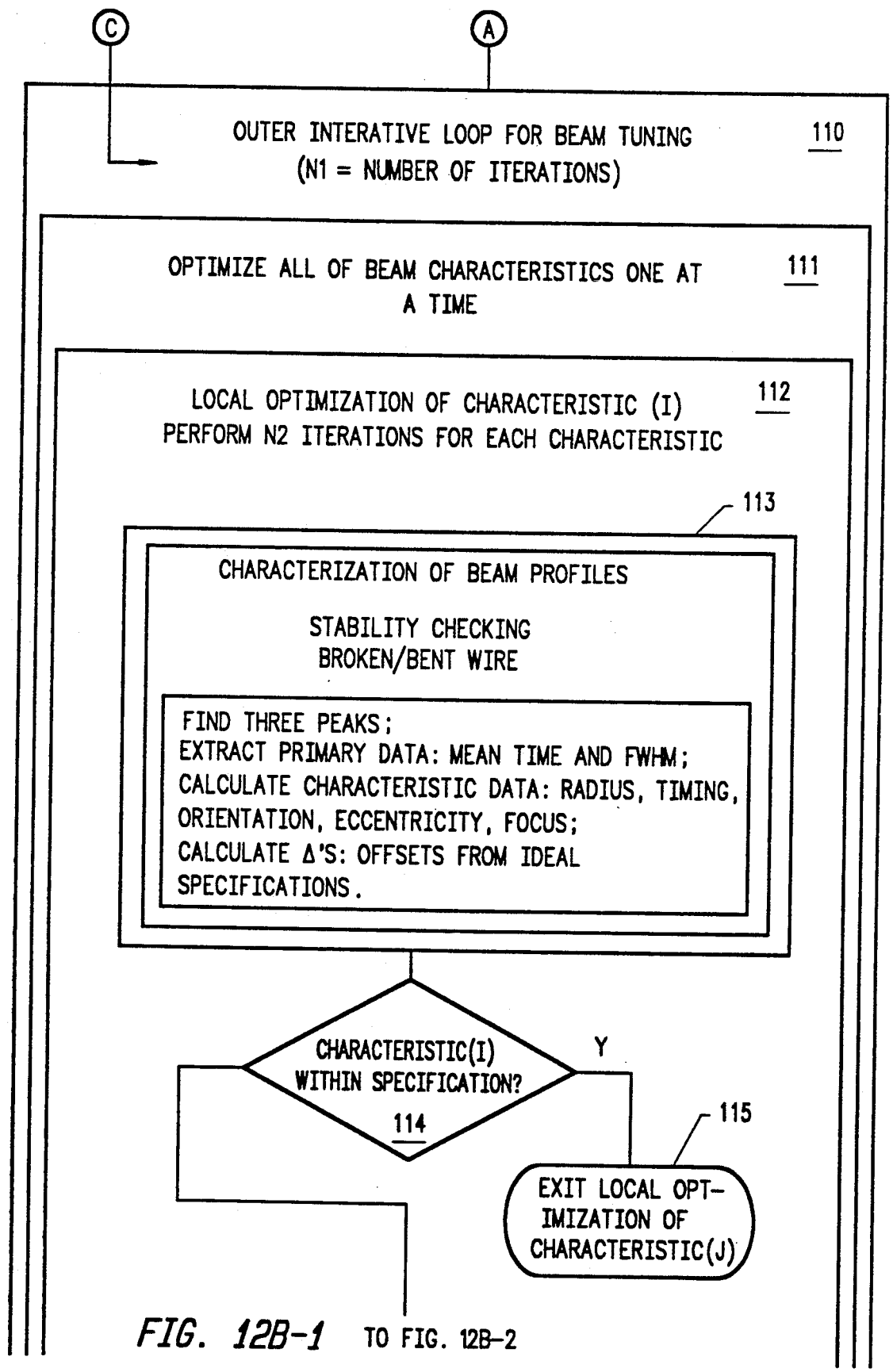
Figures 2, 12B:
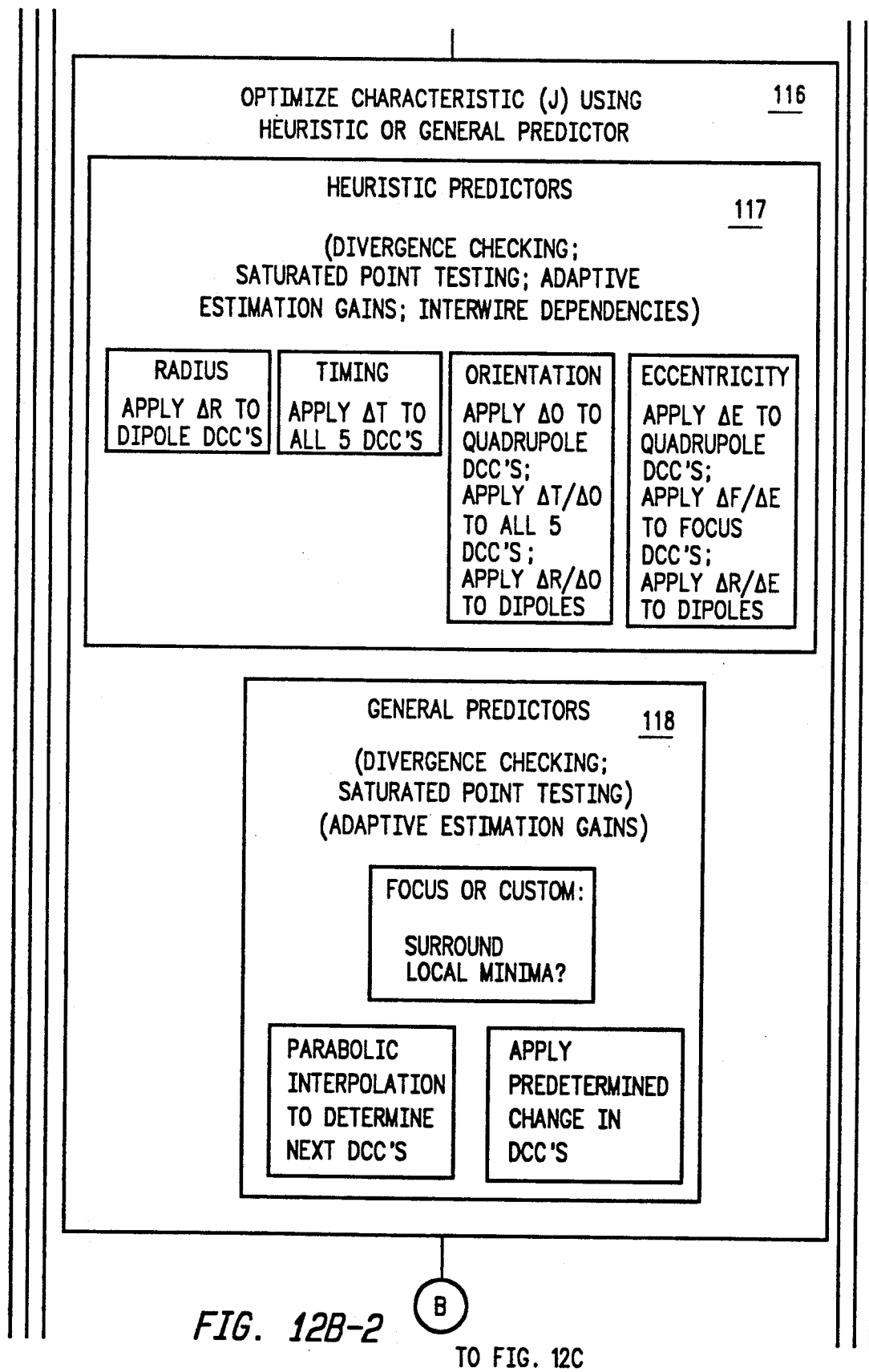

The method of controlling the electron beam is an iterative process as shown in box 110 of FIG. 12. The characteristics of the electron beam are optimized one characteristic at a time as shown in box 111. The optimization of one characteristic at a time is referred to as a local optimization and is shown in box 112. The electrical signals produced by the electron beam intercepting devices are first routed to a processing means generally indicated at 46 in FIG. 1 which includes a data acquisition system (DAS) which digitizes these signals using an analog to digital converter and stores them in memory (not shown in FIG. 12). These digitized signals are used to characterize the present state of the electron beam spot as shown in box 113. The characterization of the characteristic which is being optimized (characteristic(I)) is compared to the predetermined desired value for this characteristic. The difference between the present value of this characteristic and the desired value of this characteristic is used to compute adjustments to the deflection coil currents (DCC's) in the coils 36, 38, and 40 in the focusing and scanning arrangement 42 as shown in box 116. These computed DCC's are then loaded into the deflection system to cause the beam to conform to the desired value for this characteristic (box 119). This process continues until all of the characteristics are within the desired values and the overall state of the beam is within a desired value, or until a predetermined number of iterations have been performed.

The electron beam characterization process includes the step of finding the peaks of the electrical signals generally shown in FIGS. 5a, 5b, and 5c which are produced by the electron beam intercepting devices 52 as the electron beam sweeps over the target 30, and the step of computing the current state of the beam including radius, timing, orientation, eccentricity, and focus from these peaks. These steps are generally indicated by box 113, entitled "Characterization", in FIG. 12. Multiple sets of identical scan paths can be performed as part of the characterization process to measure the deviation in the characteristics of the beam. If the deviation in the characteristics between sets exceeds a predetermined limit, the tuning is terminated. This step is shown generally in box 113 as "Stability Checking".

Figure 11A:
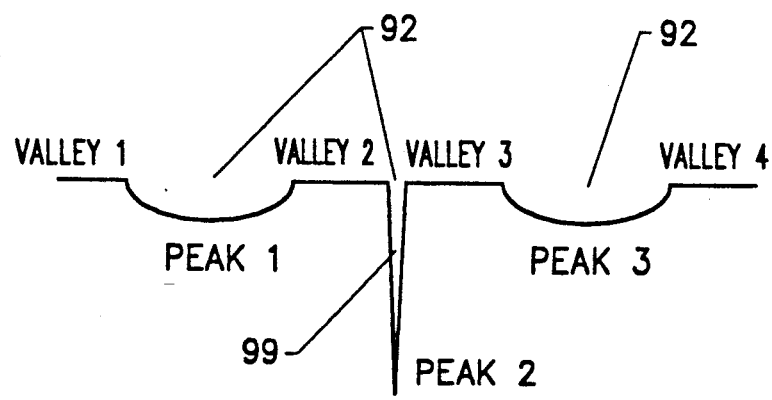
FIGS. 11a, 11b, and 11c illustrates the different shapes of electrical signals produced by the beam intercepting devices.
Figure 11B:
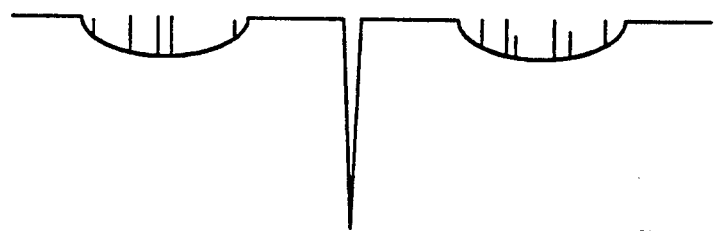

Finding the peaks of the electrical signals consists of first separating the electrical signal for each intercepting device into 3 distinct peak regions as indicated by 92 in FIG. 11a. Next, the start and end times of each of the peaks for each of the electron beam intercepting mechanisms are found. This is done by subtracting a specified noise level from the digitized electrical signals, which are stored in the processor generally indicated by reference numeral 46 in FIG. 1, and using the first and last positive data points as the endpoints of the peak. The characterization process can recognize up to two peaks in any one region for a total of six peaks. If there are more than six peaks, as shown in FIG. 11b, the data is convolved to "smooth" out the peaks until the number of peaks is six or less.

Figure 11C:
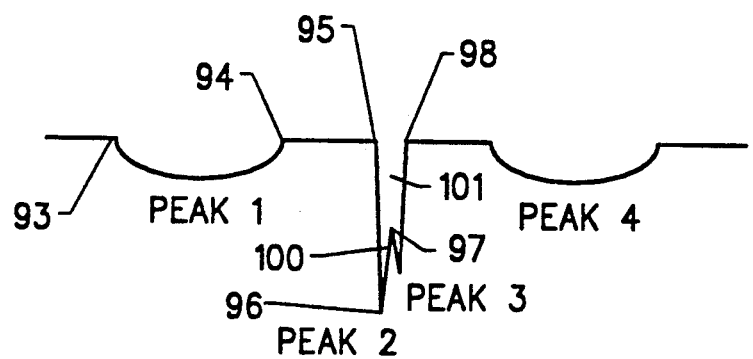

After the peaks are identified, the relative magnitudes of the valleys surrounding each peak are used to determine if the peaks are even as indicated by peak 2 in FIG. 11a, right-facing as indicated by peak 2 in FIG. 11c, or left-facing as indicated by peak 3 in FIG. 11c. A peak is classified as even, as shown by peak 1 in FIG. 11c, if the valleys 93 and 94 on either side of the peak are of equal height. The peak is classified as right-facing, as shown by peak 2 in FIG. 11c, if the valley on the right 97 is slightly higher in magnitude (more negative signal) than the valley on the left 95. The peak is classified as left-facing, as shown by peak 3 in FIG. 11c, if the valley on the left 97 is slightly higher in magnitude (more negative signal) than the valley on the right 98.

The pattern of peaks is then matched with known peak configurations. If a pattern is found, the peaks are separated into three regions, and the start and end times of each peak is stored in the processor generally indicated by 46 in FIG. 1. If no pattern is found, the convolution, peak finding, and pattern matching is repeated until the peaks are found.

The current state of the beam at each w-wire intercepting mechanism is computed using two primary characteristics of the peaks: the mean time and peak quality. The mean time represents the timing of the electron beam and the peak quality is a realistic measurement of the focus of the beam. The mean time is computed using a center-of-mass calculation for each peak which is a function of the exact location of the peak and the slope of the sides of the peak. The peak quality can be computed using the standard deviation of each peak.

The following integrals can be used to evaluate the mean time and peak quality.

$$I_0 = \int_a^b f(x)\,dx, \text{ and} \quad (1)$$

$$I_1 = \int_a^b x f(x)\,dx, \text{ and}$$

$$I_2 = \int_a^b x^2 f(x)\,dx;$$

where:
x = index (time)
f(x) = the function (beam profile value) at x
a = lower limit of x (start of peak)
b = upper limit of x (end of peak)

These integrals are evaluated for each of the peaks found by the above procedure. First, the endpoints of each peak, a, indicated in FIG. 5b by 59, and b, indicated by 61, are found. This can be done by calculating the incremental area at each point along the peak starting at the maximum value of the peak. The area can be calculated using a rectangular approximation. A summation of the total area along the peak is also calculated. If the increment is small enough, the area calculation will be accurate. The endpoints are defined as the points on each side of the maximum value of the peak at which the ratio of the incremental area and the total area falls below a specified threshold, called the incremental area ratio. Therefore, the endpoints do not have to be symmetrical about the maximum value of the peak.

The incremental area ratio can be found from the gain of the data acquisition system and the base current induced in the system between the w-wires. It has been found empirically based on the data from 2 prototype scanners that the incremental area ratio obeys the following relationship:

incremental area
ratio$_{100}$ = 9 × 10$^{-5}$ × (basecurrent) + 1.4 × 10$^{-3}$ (2)

It should be noted that this relationship may be different for different scanners.

The mean time (designated by xbar) each of the peaks can now be computed by dividing the integral $I_1$ by $I_0$, $$xbar = \frac{I_1}{I_0} = \frac{\int_a^b x f(x)\,dx}{\int_a^b f(x)\,dx} \quad (3)$$

Next, the peak quality is computed. The peak quality is defined as the full width half maximum (FWHM) of the peaks. If the peak can be approximated by an ideal shape, the FWHM can be computed from the standard deviation using a theoretical relationship. Therefore, first, the standard deviation is found using the following equation.

$$w = \sqrt{\frac{I_2}{I_0} - \left(\frac{I_1}{I_0}\right)^2} \quad (4)$$

It has been found that the central pulse 66b in FIG. 5a can be approximated with a triangle, and the side pulse 66a and 66c can be approximated with an ellipse. The relationship between the FWHM and the standard deviation for these ideal shapes is as follows:

This FWHM is a realistic measurement of the focus of the beam.

$$FWHM_w(\text{triangle}) = w\sqrt{6} = 2.449 \times w, \text{ and} \quad (5)$$

$$FWHM_w(\text{ellipse}) = 2w\sqrt{3} = 3.464 \times w$$

The characteristics of the beam at each w-wire which are used to describe the overall state of the electron beam can be calculated from these 2 primary characteristics, xbar and FWHM, of the peaks. The beam characteristics include: radius, timing, orientation, eccentricity, and focus. Radius, shown as R in FIG. 3, is a measure of the radial position of the beam on the target. It is computed as the difference of mean times between the center of the first peak (68a in FIG. 5b) and the center of the third peak (68c in FIG. 5b). Because the side prongs 56 and 58 in FIG. 5 are angled at 45°, the mean time between the third peak and the first peak are a function of the radial position of the electron beam. The radius is mainly controlled by the dipole magnets 38 shown in FIG. 9.

The mean time of the central peak is used to determine the timing of the electron beam. Timing is also mainly controlled by the dipole magnets.

As disclosed in U.S. Pat. No. 4,631,741 and indicated in FIG. 5b, the desired beam shape is an ellipse with its major axis parallel to the central wire prong 54 in FIG. 5a. The orientation of the beam spot is defined as the amount of rotation of this ellipse relative to the wire prong 54 as shown by 43 in FIG. 5c. Orientation can be computed as the difference in the FWHM of the side peaks 70a and 70c in FIG. 5c divided by the sum of these side peaks and is controlled by the quadrupole magnets 40 shown in FIG. 9.

Eccentricity represents the ratio of the major and minor axis of the elliptical beam spot. The eccentricity can be computed by taking the average FWHM of the first and third peaks 68a and 68c in FIG. 5b. Eccentricity is mainly controlled by the quadrupole magnets shown in FIG. 9.

The focus of the beam spot can be determined from the peak quality, or FWHM, of the central peak 68b in FIG. 5b if the eccentricity of the beam is correct. The focus is basically a measure of the azimuth dimension of the elliptical electron beam spot 43 in FIG. 5.

If one of the w-wire intercepting mechanisms is bent, the characteristic at that location will be offset. This offset is compensated for by calculating the ideal value that would have occurred if the wire were not bent.

The differences between the measured characteristics of the beam and the desired characteristics are used to compute the magnitude and direction of perturbations made to the electrical currents or deflection coil currents (DCC's) of the deflection system generally indicated by 36, 38, and 40 in FIG. 1. These updated DCC's "tune" the electron beam to match the desired characteristics. The present invention uses two methods for this computation: heuristic predictors and general predictors. The heuristic predictors generally indicated by box 117 in FIG. 12 change the state of the beam at a particular w-wire location by adjusting the DCC's at that particular w-wire location using a known relationship between the previous DCC's at the wire and the present characteristics of the electron beam spot. In the preferred embodiment of the present invention, the heuristic predictors are used to correct the radius, timing, orientation, and eccentricity of the electron beam spot. The general predictors generally indicated by box 118 in FIG. 12 use iterative convergence techniques to tune the scanner when these relationships are not known. In the preferred embodiment of the present invention, the general predictors are used to correct the focus of the electron beam spot.

The basic format of the heuristic predictor is as follows:

NewDCC=F(OldDCC,BeamProfileΔ*Conversion
    Constant*EstimationGain)     (6)

where:
New DCC=new deflection coil current at a particular w-wire
Old DCC=old deflection coil current at a particular w-wire
Beam Profile Delta=offset of the characteristic of the beam from the ideal specification
Conversion Constant=derived conversion between characteristic of beam and the DCC
Estimation Gain=factor to increase or decrease the amount of change in desired DCC The Beam Profile Deltas are found in the characterization process. The conversion constants are either theoretical or empirical, depending on the characteristic of interest. For example, the relationship between the orientation of the beam and the quadrupole coil current is theoretical, and the relationship between the eccentricity and the quadrupole coil currents is found empirically.

There is significant cross coupling between the characteristics predicted by the heuristic predictor. For example, a change in the eccentricity will alter the radius and focus, and a change in the orientation will alter the timing and radius of the beam. In order to reduce the effects of this cross coupling, conversion constants are used which quantify these effects. Also, corrections are made on the appropriate coil currents to minimize these effects. Also, if one of the prongs of one or more of the w-wires 52 is broken, an interpolation can be made to determine the DCC of that wire.

Features can be added to the heuristic predictors to control the changes in the characteristics of the electron beam spot as caused by the heuristic predictors. It is possible that when the state of the beam at one location is updated, for example radius at wire 2, the state of the beam at another location, for example wire 3, extends beyond a predetermined limit. When this occurs, the DCC's of the previous scan can be restored, and the appropriate estimation gain can be reduced for the next scan. If this occurs repeatedly, the scanning sequence will be terminated. This step is shown generally as "Saturated Point Testing" in the heuristic box 117 in FIG. 12. Also, if the changes in the DCC's for a particular wire or wires as predicted by the heuristic predictors exceed a predetermined limit, the estimation gain can be reduced. This step is shown generally as "Divergence Checking" in the heuristic box 117 in FIG. 12.

The process of computing the deflection coil currents to adjust the characteristics of the electron beam using the heuristic predictors is as follows:

The following variables are used in this procedure:
$\bar{X}_{peak1}$ = mean time of peak 1
$\bar{X}_{peak2}$ = mean time of peak 2
$\bar{X}_{peak3}$ = mean time of peak 3
$FWHM_{peak1}$ = full width half maximum of peak 1
$FWHM_{peak2}$ = full width half maximum of peak 2
$FWHM_{peak3}$ = full width half maximum of peak 3
*DCC = the deflection coil current associated with a certain w-wire associated with one of the beam characteristics (amps). (Where: * = radius, timing, orientation, eccentricity, or focus)
*Offset = the offset of one of the beam characteristics from the desired value ($\mu$ sec)
dx = dipole x DCC (amps) for a certain w-wire
dy = dipole y DCC (amps) for a certain w-wire
qx = quadrupole x DCC (amps) for a certain w-wire
qy = quadrupole y DCC (amps) for a certain w-wire
ft = focus trim DCC (amps)
dxpoly(t),dypoly(t),qxploy(t),qyploy(t),ftpoly(t) = polygon value of the coil of interest at time t The x and y dipole deflection coil currents to correct the radius are found as follows:

$$dx_{new}\cos = RadiusDCC_{new}\cos\theta \quad (7)$$
$$dy_{new} = RadiusDCC_{new}\sin\theta \quad (8)$$

where:

$$\theta = \tan^{-1}\left(\frac{dy_{old}}{dx_{old}}\right) \quad (9)$$

$$RadiusDCC_{new} = RadiusDCC_{old} \times \quad (10)$$
$$(1 + (radiusOffset \times RCon)) \times EstimationGain_{radius}$$

$$RCon = \frac{1}{2}\Omega\cos^2\left(\phi \times \frac{\pi}{180}\right)\left[\frac{1}{\mu sec}\right] \quad (11)$$

where:
$\Omega$ = angular speed of beam (rad/$\mu$ sec)
$\rho$ = cone angle of beam (degrees), and $$RadiusDCC_{old} = \sqrt{dx^2 + dy^2} \quad (12)$$

Figure 9:
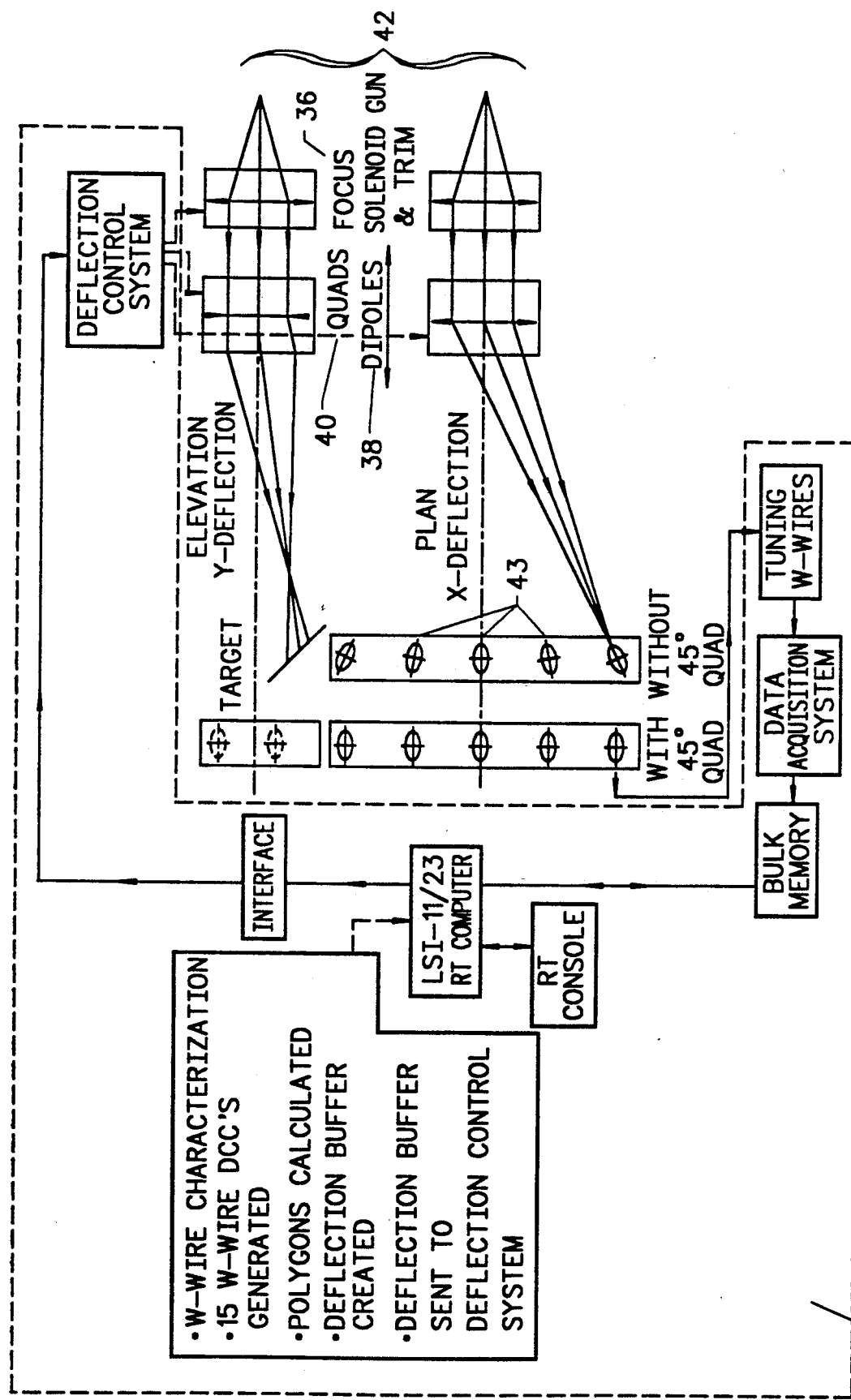
FIG. 9 shows a more detailed view of the focusing and scanning arrangement of FIG. 1 which adjusts the characteristics of the electron beam and also shows how the deflection system interacts with the computer means which calculates the electrical currents through the deflection system.

The orientation and eccentricity of the electron beam spot are controlled using the quadrupole magnets 40 in FIG. 9. Basically, the quadrupoles change the shape of the beam from a circle as defined by the focus and dipole magnets into an ellipse which maintains the same shape and orientation as the beam scans along the entire length of the target. In order to do this, the quadrupole currents vary sinusoidally with double the frequency of the dipoles.

In order to adjust the orientation and eccentricity of the beam spot, the current orientation and eccentricity of the beam are described using the following two functions. These functions are valid along the entire scan path and are defined as follows:

$$\text{Orientation}\mu sec = (\text{FWHM}_{peak3} - \text{FWHM}_{peak1}) + (\text{FWHM}_{peak3} + \text{FWHM}_{peak1}) \quad (13)$$

$$\text{OrientationDCC} = (qx - qxoff) \times \sin\theta - (qy - qyoff) \times \cos\theta \quad (14)$$

$$\text{Eccentricity}\mu sec = (\text{FWHM}_{peak1} + \text{FWHM}_{peak3}) \div 2 \quad (15)$$

$$\text{EccentricityDCC} = -(qx - qyoff) \times \cos\theta - (qy - qyoff) \times \sin\theta - qdip \quad (16)$$

where:
qxoff = quad x offset;
qyoff = quad y offset
$\theta = 2 *$ wire angle + quad phase lag;
qdip = quad eccentricity due to dipoles Specifically, the coil currents required to alter the orientation of the beam can be calculated as follows:

First, calculate the angular shift required to straighten the beam:

$$\theta_{all} = \tan^{-1}(\text{Orientation}_{\mu sec}) \quad (17)$$

The original angle of the beam is represented by:

$$\theta_{ini} = \tan^{-1}\left(\frac{\text{Orientation}DCC_{old}}{\text{Eccentricity}DCC_{old}}\right) \quad (18)$$

The initial quadrupole magnitude is:

$$qmag = \sqrt{\text{Orientation}DCC_{old}^2 + \text{Eccentricity}DCC_{old}^2} \quad (19)$$

The new angular shift needed to straighten the beam can now be computed as:

$$\theta_{new} = \theta_{ini} + (2 \times \theta_{all} \times \text{EstimationGain}_{quad}) \quad (20)$$

The factor of 2 is due to the quadrupoles varying at twice the angular frequency as the dipole beam deflection. The new orientation deflection coil current becomes:

$$\text{OrientationDCC}_{new} = qmag \times \sin(\theta new) \quad (21)$$

The new qx and qy values are derived from the original eccentricity (Equation 15) and the new orientation as calculated by Equation 21.

This change in orientation affects the timing and the radius and these changes must be accounted for. The radius and timing change due to the change in orientation are computed as follows:

$$\text{Timing}_{new} = (\text{Orientation}DCC_{new} - \text{Orientation}DCC_{old}) \times \frac{del\text{Timing}}{del\text{Orientation}} \quad (22)$$

$$\text{Radius}_{new} = (\text{Orientation}DCC_{new} - \text{Orientation}DCC_{old}) \times \frac{del\text{Radius}}{del\text{Orientation}} \quad (23)$$

where:
delTiming/delOrientation = change in timing per change in orientation
delRadius/delOrientation = change in radius per change in orientation The eccentricity is computed in a manner similar to that for radius. Specifically, the new DCC is calculated as:

$$\text{Eccentricity}DCC_{new} = \text{Eccentricity}DCC_{old} + (\text{Eccentricity}_{\mu sec} \times \text{ECon} \times \text{EstimationGain}_{ECC}) \quad (24)$$

where:
ECon = eccentricity conversion factor = constant

The eccentricity is coupled with the radius and the focus. The radius and focus change due to the change in eccentricity are computed as follows: where:
FocusDCC = focus trim doc
DelEll = EccentricityDCC$_{new}$ − EccentricityDCC$_{old}$)

$$\text{Radius}DCC_{new} = \text{Radius}DCC_{old} + \left(DelEll \times \frac{del\text{Radius}}{del\text{Eccentricity}}\right) \quad (25)$$

$$\text{Focus}DCC_{new} = \text{Focus}DCC_{old} + \left(DelEll \times \frac{del\text{Focus}}{del\text{Eccentricity}}\right) \quad (26)$$

delRadius/delEccentricity = change in radius per change in eccentricity
delFocus/delEccentricity = change in focus trim per change in eccentricity In addition, cross-dependencies between the wires are quantized and compensations are made to reduce their effects.

The timing is not adjusted by updating the DCC's. Rather, the angular speed of the beam is adjusted by assigning to the DCC's of each coil interpolated values at discrete instants in time. These interpolated values are derived by fitting a continuous curve through the DCC values at the w-wire locations 52 FIG. 3. This curve is then broken up into a series of discrete values called polygon sides. A more detailed description of the computation of these polygon values is found below. By setting the DCC's for each coil to the interpolated polygon value at these discrete instants in time, the beam will arrive at the correct time with approximately the same state. The state of the beam at the time that the beam should have hit the center wire 54 FIG. 5 is derived from the polygons and is loaded as the new DCC value for that particular w-wire. This optimization may have to be repeated a few time before converging since the new DCC's are not found by any single known conversion for the coils. The general equation for the timing of any of the coils is:

dx = dx$_{poly}$ (−TimeOffset);

dy = dy$_{poly}$ (−TimeOffset);

$$qx = qx_{poly}(-\text{TimeOffset});$$

$$qy = qy_{poly}(-\text{TimeOffset});$$

$$ft = ft_{poly}(-\text{TimeOffset}); \quad (27)$$

If the $-$TimeOffset does not occur on an actual polygon vertex, the value at $-$TimeOffset is interpolated between the two nearest neighbors.

The focus of the electron beam can be adjusted by using general predictors, box 118 FIG. 12, which make incremental changes in the DCC's at each w-wire in an iterative fashion. The direction of the subsequent iteration is in the direction of most improvement. A parabolic iteration is useful in optimizing the focus by optimizing the peak quality of the central peak. The iteration described in Section 10.2 of *Numerical Recipes in C: The Art of Scientific Computing* (Flannery, Teukolsky, and Vetterling, 1989) could be used. Changes in the focus solenoid deflection coil current change the focus value at all of the w-wire locations. If a global change in focus is desired, the focus solenoid deflection coil current can be changed to change the focus along the entire path. This procedure is more efficient than changing the focus deflection coil current at every w-wire location. It is also possible to optimize the other characteristics of the beam such as radius, orientation, and eccentricity using general predictors.

General predictors can also be used to speed up the optimization process by analyzing the overall improvement made by the heuristic predictors. A general predictor called a custom vector creates a vector of changes of all 5 of the DCC's based on the heuristic optimizations and minimizes the offsets from the ideal specifications of all 5 characteristics of the beam simultaneously. The improvement resulting from this step can be measured with an appropriate judgement function. The magnitude of this custom vector may be scaled such that a single step will not exceed a predetermined amount. This is especially important when controlling the radius, because it is possible that too large a change in the radius will cause the electron beam to completely miss the w-wires. Additional improvements may be possible by executing a single general optimization.

Using the desired coil currents at the w-wires as computed above using either the heuristic or general methods, a continuous curve that directs the flow of current through each of the 5 magnets over the entire scan path is computed. This continuous curve 86 in FIG. 10 includes the beam-stop holding path 80, the on-path 87, target path 83, and the off-path 88. The electron beam remains at the holding path when the beam is not scanning along the target. The on-path lies between the holding path and the target-path. The off-path lies between the target path and the holding path.

First, the continuous curve on the target path 83 is computed. Since the w-wire monitoring devices do not completely cover the entire target path of the electron beam, interpolation is used to describe the coil currents between these monitoring devices. The first step is to fit curves through the desired currents at each of the w-wire locations along the target path. Next, a continuous curve is found which passes through all of these individual curves. This continuous curve is then divided up into discrete values that are used to update all of the coil currents at known timing intervals.

The process of fitting curves through each of the w-wire locations consists of fitting an ellipse through every unique group of 3 consecutive w-wires along the scan path 48 FIG. 3. This results in N-2 ellipses for N w-wires. Therefore, a total of 13 ellipses are derived for the 15 w-wire intercept mechanisms 52 in FIG. 3. The ellipses are derived to satisfy the following form:

$$x(t) = A + B \cos \omega t + C \sin \omega t \quad (28)$$

where:
x(t) = coil current at time t for a particular magnet
$\omega$ = angular speed of the beam over the scan path
A,B,C = derived coefficients
For the three consecutive wire currents at times $t_1$, $t_2$, $t_3$, the following matrix is solved:

$$\begin{vmatrix} \cos(\omega t_1) & \sin(\omega t_1) \\ \cos(\omega t_2) & \sin(\omega t_2) \\ \cos(\omega t_3) & \sin(\omega t_3) \end{vmatrix} \times \begin{vmatrix} A \\ B \\ C \end{vmatrix} = \begin{vmatrix} x(t_1) \\ x(t_2) \\ x(t_3) \end{vmatrix} \quad (29)$$

Checks are made to avoid singularity problems.

Next, a continuous curve on the on-path is calculated. The on-path 87 is separated into two regions called the "onpath" 81 FIG. 10 and the "leeon" 82. The onpath spans from the holding path towards the target path and the leeon spans from the target path backwards toward to the onpath. The curve describing the coil currents along the leeon are found by extrapolating the coil current backwards toward the holding path using the derived ellipse that spans through w-wire 1, 2, and 3. The continuous curve from the holding path to the leeon is found by fitting a cubic, as defined by the following equation, between the holding path and the start of the leeon.

$$x(t) = A(t - t_{hp})^2(t - t_{leeon}) + B(t - t_{hp})^2 + C(t - t_{hp}) + D(t - t_{leeon}) \quad (2)$$

It is also possible to fit a cubic directly between the holding path and the target path, using the values and time derivatives at each end.

Figure 10:
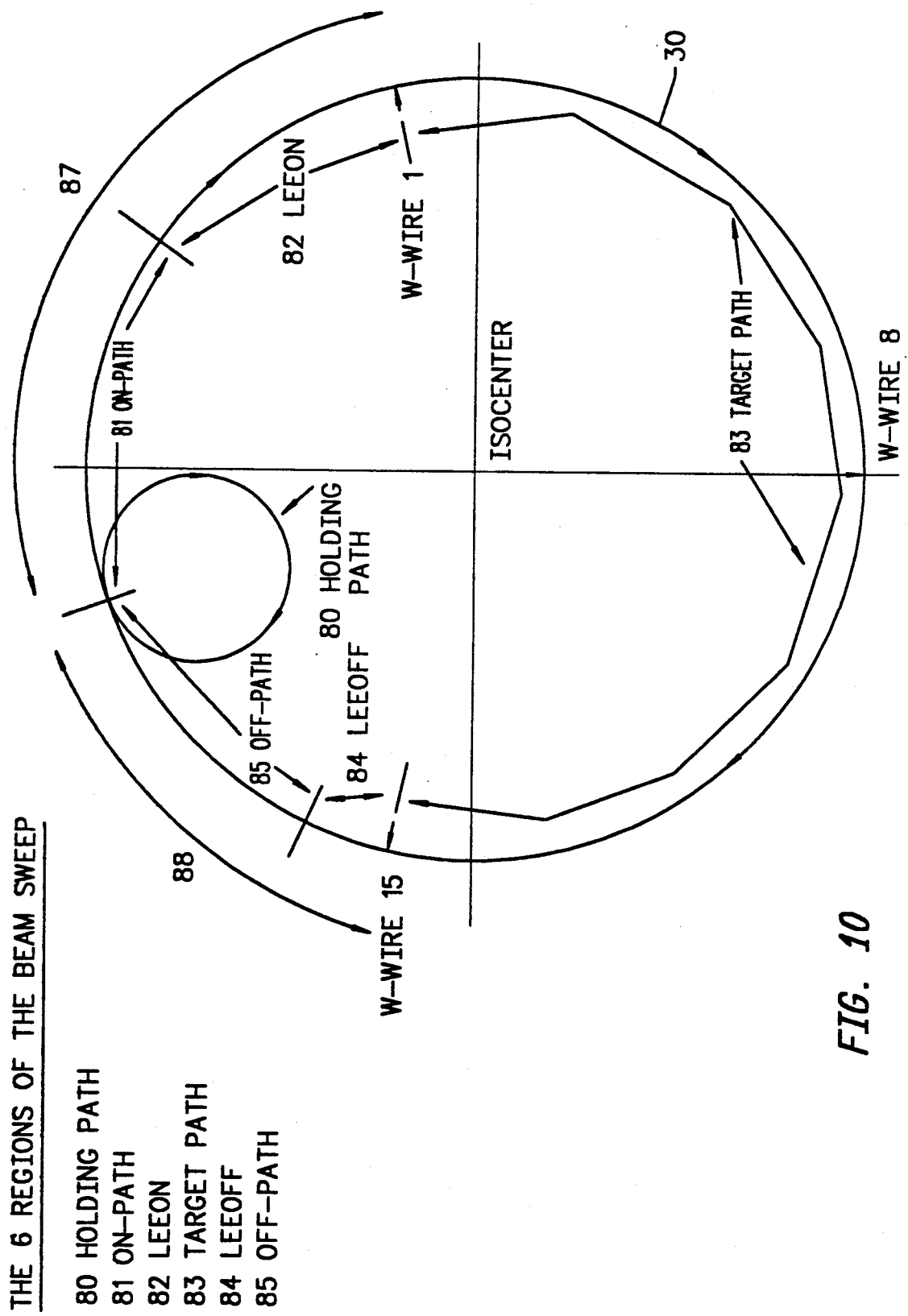
FIG. 10 illustrates the specific regions of the electron beam scan path.

The off-path 88 is similarly broken into two regions called the leeoff 84 in FIG. 10 and the offpath 85. The off-path calculations are similar to the on-path calculations. The ellipse through wires 13, 14, and 15 are extrapolated from the target path to leeoff and a cubic is fit between the leeoff and the holding path.

The ellipses and curves computed above are used as guides to compute a continuous curve of coil currents along the entire length of the electron beam scan path. This continuous curve actually consists of values for the coil currents for the 5 magnets at discrete instances in time along the entire electron beam scan path. These discrete values are computed by fitting a polygon (typically with 122 sides) to the ellipses and curves described above.

The polygon for the target path is computed by using a set of joint functions to ensure that the slope and value at each intersection of the polygon sides match. These joint functions are:

$$h(t) = \frac{1}{2}\left(1 + \cos\left(\frac{t - t_1}{t_2 - t_1}\right)\pi\right) \quad (31)$$

-continued
$$k(t) = 1 - h(t) \tag{32}$$

where:
$t_1$ = time at w-wire i;
$t_2$ = time at w-wire i+1;
$h(t_1)=1$, $k(t_1)=0$; $h'(t_1)=k'(t_1)=0$;
$h(t_2)=0$, $k(t_2)=1$; $h'(t_2)=k'(t_2)=0$;

The values of ellipse j at each polygon intersection between wire i and i+1 is evaluated and loaded into one buffer and another buffer is loaded with the values of ellipse j+1 at the same polygon intersections. The first buffer is multiplied by h and the second by k, then they are summed to find the value of the polygon at each time t.

The on-path and off-path polygon values are the values described by the cubic or extrapolated ellipse at each of the on-path or off-path points.

The DCC values for each of the polygon sides are then loaded into the deflection buffer which is used to drive the flow of current through the magnets in the deflection system. This process is generally indicated in box 119 of FIG. 12 entitled "Scan Sever". The values in the deflection buffer are then multiplied by the gain and offset of the corresponding magnets. In order to allow for the deflection system to update the coil currents at a rate greater than the rate at which the polygon sides describe the currents, the deflection buffer is loaded with the actual values and the increments or slopes needed to achieve the next value in the time allotted. A linear fit is used to describe these increments. Therefore, the deflection buffer consists the following data:

$$Dx\ Dy\ Qx\ Qy\ F\ Dx_{inc}\ Dy_{inc}\ Qx_{inc}\ Qy_{inc}\ F_{inc}$$

where:
Dx = dipole x DCC (amps)
Dy = dipole y DCC (amps)
Qx = quadrupole x DCC (amps)
Qy = quadrupole y DCC (amps)
F = focus trim DCC (amps)
$Dx_{inc}$ = incremental value of dipole x DCC (amps)
$Dy_{inc}$ = incremental value of dipole y DCC (amps)
$Qx_{inc}$ = incremental value of quadrupole x DCC (amps)
$Qy_{inc}$ = incremental value of quadrupole y DCC (amps)
$F_{inc}$ = incremental value of focus trim DCC (amps)

The estimation gain from Equation 6 can be modified to adjust for the differences between the actual changes in the beam characteristics caused by the new deflection coil currents and the predicted changes in the beam characteristics. This step is shown generally in box 117 of FIG. 12 as "Adaptive Estimation Gain".

In a preferred embodiment of the present invention, the quality of the tune is quantitatively defined. This quality can be on a wire-by-wire, path, or whole tune basis. A path consists of one sweep across all of the w-wires, and whole tune consists of any number of these paths. The quality function or defect function of a single wire is represented by F and has the format:

$$F = \left( \frac{1}{k_R + k_T + k_\Omega + k_E + k_F} \right) *$$ (33)

$$\left\{ k_R \left( \frac{\delta R}{\Delta R} \right)^{2n} + k_T \left( \frac{\delta T}{\Delta T} \right)^{2n} + k_\Omega \left( \frac{\delta \Omega}{\Delta \Omega} \right)^{2n} + \right.$$

-continued
$$\left. k_E \left( \frac{\delta E}{\Delta E} \right)^{2n} + k_F \left( \frac{\delta F}{\Delta F} \right)^{2n} \right\}$$

where:
n = integer
k = weighting factors for the different characteristics;
$\delta R$ = offset of radius from ideal specifications;
$\Delta R$ = allowed deviation in radius from ideal specifications;
$\delta T$ = offset of timing from ideal specifications;
$\Delta T$ = allowed deviation in timing from ideal specifications;
$\delta \Omega$ = offset of orientation from ideal specifications;
$\Delta \Omega$ = allowed deviation in orientation from ideal specifications;
$\delta E$ = offset of eccentricity from ideal specifications;
$\Delta E$ = allowed deviation in eccentricity from ideal specifications;
$\delta F$ = offset of focus from ideal specifications;
$\Delta F$ = allowed deviation in focus from ideal specifications.

This function will be less than 1 if all of the characteristics are within allowable specifications, and greater than 1 if out of specification. This F-factor can be summed for each of the w-wires in order to get a path or whole tune F-factor. A wire quality factor, WQF, and a summary quality factor, SQF, can be defined as:

$$WQF = \frac{k_{WQF}}{F} \tag{34}$$

for an individual wire, or $$SQF = \sum_{i=1}^{n} \frac{k_{WQF}}{F_i} \tag{35}$$

for an entire path (n = 15k wires) or whole tune (typically n = 30k wires), where k is the number of scan paths considered.

where:
$k_{WQF}$ is a normalization factor for the summary quality factor.
$F_i$ is the quality function for wire i.

This quality factor will therefore increase as the tune approaches ideal specifications. If a drastic degradation occurs in the summary quality factor, the changes in the quality functions of the individual wires can be analyzed to determine possible reasons for the degradation.

The procedure described by the present invention can be implemented as a computer program which can operate autonomously without any input from the user. The operator initiates the program, and some very brief messages appear on the screen to let the user know that the code is operating, and the scanner will pulse the beam about every 30 seconds until tuning is completed. After completion, a message will be shown on the screen telling the user whether or not the tune is acceptable for scanning, and some additional information is available in an error log if the user is interested. Additional tracing files are created and can be used for inspection.

Basically, the procedure is broken into three parts: preliminary tests, local optimization, and global optimization. In the preliminary tests, the general state of the beam is determined as shown in box 105 of FIG. 12.

Predetermined DCC's are loaded into the deflection system 42 and the electron beam is pulsed. The resulting beam characteristics are analyzed to determine the sensitivity of the scanner to changes in the DCC's and to determine if the changes in the characteristics due to the DCC's are acceptable. These steps are labeled as "Preliminary Sensitivity Test" and "Overfocus Test" in box 105. Also, the preliminary tests check to see if the beam is overfocused. The beam is overfocused if the focus in the azimuthal plane reaches a predetermined minimum value. This test is labeled as "Preliminary Control Test" in box 105.

The local optimization, generally indicated by box 112 in FIG. 12, controls the optimization of a single characteristic (timing, for example). It will continue to optimize the appropriate characteristic using the heuristic (box 117) or general predictor (box 118) until the characteristic of interest is within specifications (box 114) or a certain number of iterations has been completed (N2 in box 112). After each iteration in the local optimization box 112, the updated deflection coil currents as calculated in the predictor algorithm (box 116) are loaded into the deflection system to adjust the state of the electron beam (box 119). This box is referred to as the Scan Server. The Scan Server also includes the DAS which collects and digitizes the w-wire data. The Scan Server also contains several sanity checks to ensure that the system is operating correctly. The hardware state of the scanner 10 is constantly checked to ensure that the components are operating satisfactorily. This step is labeled as Hardware Checks in box 119. The high-voltage power supply 19 is ramped down every 15 minutes to ensure that the power supply is in the desired state. If errors occur during the scan, the Scan Server will repeat the scan. If errors still exist, the program will terminate. These errors include power supply errors, DAS errors, electron beam errors, etc.

The DAS data is used by the characterization algorithms to compute the effect of these updated DCC's on the characteristics of the electron beam (box 113). The quality factor and F-factor are allowed to deteriorate within a local optimization, as the predictors might not be completely independent (as mentioned in the description of the heuristic predictors). The electron beam characteristic to be optimized by a given local optimization is chosen by one of two global optimization strategies: it can be either list-driven, where the characteristics are stepped through according to their order on a list; or it can be offset driven, where the optimization is chosen based on which characteristic is the farthest away from meeting specification. After each local optimization of each characteristic, a new best state can be stored based on the current state if the overall quality of the current state reflects an improvement over the previous best state (box 120, 121).

After a series of these local optimizations, the global optimization software, generally indicated by box 127 in FIG. 12, will decide if the whole tune quality is within predetermined specifications (box 122). If it is, tuning will be completed (box 124). If not, program will check if the overall quality of the beam has improved (box 123). If the state of the tune has improved, this new state is stored into the appropriate active control files (box 126) and tuning is continued (box 128). If the overall quality of the beam has not improved, tuning will be completed (box 124). Tuning will also be completed after a maximum number of iterations (N1 in box 110). At the end of every tuning session, the tune is compared to specifications and a report issued to the user indicating if the tune is acceptable for scanning or not (box 125). If the tune is unacceptable, the user will be informed of some possible reasons why the tune did not meet specifications, if such possible reasons are known, during normal scanner operation.

It should be further apparent to those skilled in the art that various changes in form and details of the invention as shown and described may be made. It is intended that such changes be included within the spirit and scope of the claims appended hereto.

What is claimed is:

1. A scanning electron beam computed tomography scanner including means defining a vacuum chamber, means for producing an electron beam at one location in said chamber and for directing said electron beam to a second location therein, a target located at a third position therein of the type which produces X-rays as a result of the impingement thereon by said electron beam, adjustable means for focusing the beam onto said target in the form of a beam spot and for scanning said beam spot across the target along a particular scan path in order to produce X-rays which are directed upward towards detector means, and means for monitoring the profile, position, and orientation of said beam spot at a plurality of locations along said scan path, said monitoring means comprising electron beam intercepting arrangements located at said locations along said scan path which produce electrical signals upon impingement by said electron beam such that the configuration of said signals vary with the profile, position, and orientation of said beam spot, said configuration of said signals being used to monitor said beam spot, the improvement comprising:
   (a) means for determining from said characterization if said beam spot conforms to a desired profile, position, and orientation;
   (b) means for computing adjustments to said focusing and scanning means to cause the profile, position, and orientation of said electron beam to conform to desired values; and
   (c) means for defining quantitatively the overall quality of said electron beam spot along said scan path.

2. The apparatus as in claim 1 wherein said characterizing means, determining means, computing means, and defining means function automatically.

3. The improvement as in claim 1 wherein said determining means includes means for digitizing said electrical signals and means for storing said digitized signals.

4. The improvement as in claim 1 wherein said scanner further includes means for displaying said electrical signals on a video screen.

5. The improvement as in claim 1 wherein said determining means includes means for quantitatively defining the current state of said electron beam using said electrical signals.

6. The improvement as in claim 5 wherein said defining means further includes means for computing the start and end times of said electrical signals.

7. The improvement as in claim 5 wherein said defining means further includes means for matching the patterns of said electrical signals with known patterns of said electrical signals.

8. The improvement as in claim 5 wherein said defining means further includes means for computing the timing of said electrical signals using the following equation:

$$\text{mean time} = \frac{\int_a^b t f(t) \, dt}{\int_a^b f(t) \, dt}$$

where:
a = start time of electrical signal
b = end time of electrical signal
f(t) = function representing electrical signal (current) with respect to time
t = time 9. The improvement as in claim 5 wherein said defining means further includes means for computing the quality of the electrical signal.

10. The improvement as in claim 9 wherein said computing means includes means for:
(1) computing the width of said electrical signal;
(2) approximating said electrical signal as an ideal shape; and
(3) computing said quality of said electrical signal as a function of said width whereby said function varies with said ideal shape.

11. The improvement as in claim 5 wherein said defining means further includes:
means for computing the quality of the electrical signal;
means for computing the timing of said electrical signals using the following equation:

$$\text{mean time} = \frac{\int_a^b t f(t) \, dt}{\int_a^b f(t) \, dt}$$

where:
a = start time of electrical signal
b = end time of electrical signal
f(t) = function representing electrical signal (current) with respect to time
t = time; and further includes
means for computing from said quality and timing of said electrical signals at said locations the characteristics of said electron beam at said locations.

12. The improvement as in claim 11 wherein said characteristics of said electron beam spot further include the radius, timing, orientation, eccentricity, and focus.

13. The improvement as in claim 11 wherein said radius of said electron beam is computed by taking the difference of said timing of said electrical signals associated with one of said electron beam intercepting arrangements.

14. The improvement as in claim 11 wherein said timing of said electron beam is computed as a function of said timing of said electrical signals and a specified reference time.

15. The improvement as in claim 11 wherein said orientation of said electron beam is computed as a function of said width of said electrical signals.

16. The improvement as in claim 11 wherein said eccentricity of said electron beam is computed as a function of said width of said electrical signals.

17. The improvement as in claim 11 wherein said focus of said electron beam is computed as a function of said width of said electrical signals.

18. The improvement as in claim 1 wherein said determining means further includes means for quantitatively computing the offset of said characteristics of said electron beam spot from the desired values of said characteristics of said electron beam spot.

19. The improvement as in claim 1 wherein said focusing and scanning means includes dipole magnets, quadrupole magnets, focus coils, focus solenoids, or any combination thereof.

20. The improvement as in claim 1 wherein said focusing and scanning means is an electrical field focusing device.

21. The improvement as in claim 1 wherein said computing means further includes means for computing the magnitudes and directions of the electrical currents through said focusing and scanning means, said computed currents causing said radius, timing, orientation, and eccentricity of said electron beam spot to conform to the desired radius, timing, orientation, eccentricity, and focus.

22. The improvement as in claim 21 wherein said electrical currents are associated with one of said electron beam intercepting arrangements.

23. The improvement as in claim 21 wherein said computing means utilizes a known functional relationship between the electrical currents in said focusing and scanning means and said radius, timing, orientation, and eccentricity of said electron beam spot.

24. The improvement as in claim 21 wherein said computing means utilizes iterative techniques.

25. The improvement as in claim 21 wherein said computing means includes means for quantifying the cross coupling effects between said characteristics of said electron beam spot, and means for correcting said electrical currents through said focusing and scanning means such that said cross coupling effects are minimized.

26. The improvement as in claim 21 wherein said computing means further includes iterative means for computing said electrical currents in said focusing and scanning means.

27. The improvement as in claim 26 wherein said iterative means further includes means for minimizing offsets of said characteristics of said electron beam spot simultaneously.

28. The improvement as in claim 27 wherein said iterative means further includes means for preventing the change in each of said characteristics from exceeding a predetermined amount in each step of iterative process.

29. The improvement as in claim 5 wherein said defining means further includes means for defining quantitatively the quality of said electron beam spot at one of said electron beam intercepting arrangements.

30. The improvement as in claim 1 wherein said defining means further includes means for defining quantitatively the quality of said electron beam spot along said scan path.

31. The improvement as in claim 1 wherein said defining means further includes means for defining quantitatively the quality of said electron beam spot along a plurality of said scan paths.

32. The improvement as in claim 29 wherein said quality is defined using the following equation:

$$F = \left(\frac{1}{k_R + k_T + k_\Omega + k_E + k_F}\right) *$$

$$\left\{ k_R \left(\frac{\delta R}{\Delta R}\right)^{2n} + k_T \left(\frac{\delta T}{\Delta T}\right)^{2n} + k_\Omega \left(\frac{\delta \Omega}{\Delta \Omega}\right)^{2n} + \right.$$

$$\left. k_E \left(\frac{\delta E}{\Delta E}\right)^{2n} + k_F \left(\frac{\delta F}{\Delta F}\right)^{2n} \right\}.$$

33. The improvement as in claim 1 wherein said computing means further includes means for computing a continuous set of electrical currents through said focusing and scanning means from said electrical currents associated with said electron beam intercepting arrangements, said continuous set of electrical currents directing said electron beam along said scan path with said desired characteristics of said electron beam spot.

34. The improvement as in claim 33 wherein said scan path includes a beam stop holding path, an on-path, a target path, and an off-path.

35. The improvement as in claim 33 wherein said computing means further includes means for (1) fitting individual curves through the said desired electrical currents associated with said electron beam intercepting arrangements, (2) forming a continuous curve through all of said individual curves, and (3) computing from said continuous curve a set of discrete values, said discrete values representing the electrical currents through said focusing and scanning means at predetermined instants in time.

36. The improvement as in claim 35 wherein said individual curves along said target path are ellipses passing through three consecutive said electron beam intercepting arrangements, said ellipse being of the form:

$$x(t) = A + B \cos \omega t + C \sin \omega t$$

where:
x(t) = electrical current at time t
$\omega$ = angular speed of electron beam over scan path
A, B, C = derived coefficients.

37. The improvement as in claim 35 wherein said scan path includes an on-path, and wherein said individual curves along said on-path are extrapolated cubic equations.

38. The improvement as in claim 35 wherein said scan path includes an off-path, and wherein said individual curves along said off-path are extrapolated cubic equations.

39. The improvement as in claim 35 wherein said forming means further includes means for (1) breaking said scan path into discrete sections, (2) computing values of said electrical currents at said discrete sections using said individual curves, and (3) ensuring that said values of said electrical currents that are adjacent are compatible.

40. The improvement as in claim 35 wherein said computing means further includes means for using an incremental electric current between said discrete values.

41. The improvement as in claim 30, wherein said quality is defined using the following equation:

$$F = \left(\frac{1}{k_R + k_T + k_\Omega + k_E + k_F}\right) *$$

$$\left\{ k_R \left(\frac{\delta R}{\Delta R}\right)^{2n} + k_T \left(\frac{\delta T}{\Delta T}\right)^{2n} + k_\Omega \left(\frac{\delta \Omega}{\Delta \Omega}\right)^{2n} + \right.$$

$$\left. k_E \left(\frac{\delta E}{\Delta E}\right)^{2n} + k_F \left(\frac{\delta F}{\Delta F}\right)^{2n} \right\}.$$

42. The improvement as in claim 31 wherein said quality is defined using the following equation:

$$F = \left(\frac{1}{k_R + k_T + k_\Omega + k_E + k_F}\right) *$$

$$\left\{ k_R \left(\frac{\delta R}{\Delta R}\right)^{2n} + k_T \left(\frac{\delta T}{\Delta T}\right)^{2n} + k_\Omega \left(\frac{\delta \Omega}{\Delta \Omega}\right)^{2n} + \right.$$

$$\left. k_E \left(\frac{\delta E}{\Delta E}\right)^{2n} + k_F \left(\frac{\delta F}{\Delta F}\right)^{2n} \right\}.$$

43. A method of controlling an electron beam in a scanning electron beam computed tomography scanner comprising means defining a vacuum chamber, means for producing an electron beam at one location in said chamber and for directing said electron beam to a second location therein, a target located at a third position therein of the type which produces X-rays as a result of the impingement thereon by said electron beam, adjustable means for focusing the beam onto the target in the form of a beam spot and for scanning said beam spot across the target along a particular scan path in order to produce X-rays which are directed upward towards detector means, means for monitoring the profile, position, and orientation of said beam spot at a plurality of locations along said scan path, said monitoring means comprising electron beam intercepting arrangements located at said locations along said scan path which produce electrical signals upon impingement by said beam such that the configuration of said signals vary with the profile, position, and orientation of said beam spot, said configuration of said signals being used to monitor said beam spot, comprising the steps of:

(1) characterizing the profile, position, and orientation of said electron beam spot;

(2) determining from said signals if said beam spot conforms to a desired profile, position, and orientation;

(3) computing adjustments to said focusing and scanning means to cause the profile, position, and orientation of said electron beam conform to desired values; and (4) defining quantitatively the overall quality of said electron beam spot along said scan path.

44. The method as in claim 43 wherein said method is performed automatically.

45. The method as in claim 43 further including the following steps: (1) optimizing one of said characteristics of said electron beam spot in an iterative process until said characteristic is within predetermined specifications or until a predetermined number of iterations have been performed, (2) deciding whether overall quality of said electron beam spot has increased or decreased after the optimization of each of said characteristics, (3) optimizing overall quality of said electron beam in an iterative process, (4) completing said process if overall quality of said beam spot is within predetermined values or if a predetermined number of iterations have occurred, (5) creating a report indicating whether overall quality of said electron beam is within said predetermined specifications, and (6) indicating in said report the reasons why said overall quality of said electron beam was not within said predetermined specifications.

46. The method as in claim 45 wherein said steps are performed automatically.

47. The method as in claim 43 wherein said means for focusing and for scanning is responsive to electrical currents, and further including the step of resetting said electrical currents through said focusing and scanning means to their previous values if one of said characteristics is outside said predetermined specifications.

48. The method as in claim 45 including the steps of pulsing said electron beam at a predetermined frequency.

49. The method as in claim 43 further including the step of determining if said electron beam is overfocused.

50. The method as in claim 43 further including the step of constantly checking for defects in components comprising said scanner.

51. The method as in claim 43 further including the steps of quantifying cross coupling effects between said electron beam intercepting arrangements.

52. The method as in claim 43 further including the step of determining if one or more of said electron beam intercepting arrangements is broken.

53. The method as in claim 43 further including the step of correcting said electric signals associated with said electron beam intercepting arrangements if said electron beam intercepting arrangements is bent.

54. A method of controlling an electron beam in a scanning electron beam computed tomography scanner that includes electron beam intercepting arrangements disposed along the electron beam scan path, the method including the step of defocusing the electron beam during scans which are not used for creating images in order to prevent damage to said electron beam intercepting arrangements.

55. A method of controlling an electron beam in a scanning electron beam computed tomography scanner including the steps of: (1) performing a plurality of identical scans with the electron beam across a target, (2) computing deviation of said electron beam's characteristics, (3) comparing said deviation to a predetermined range, and (4) halting said scan if said deviation is not within said predetermined range and continuing said scan if said deviation is within said predetermined range.

56. A method of controlling an electron beam in a scanning electron beam computed tomography scanner that includes scanning and focusing means responsive to electrical currents, the method including the step of quantifying effects of changing said electric currents in said scanning and focusing means upon characteristics of said electron beam.

* * * * *